United States Patent
Uchimura (10) Patent No.: US 11,224,329 B2
(45) Date of Patent: Jan. 18, 2022

(54) MEDICAL OBSERVATION APPARATUS

(71) Applicant: Sony Olympus Medical Solutions Inc., Tokyo (JP)

(72) Inventor: Sumihiro Uchimura, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/917,926

(22) Filed: Jul. 1, 2020

(65) Prior Publication Data
US 2020/0329949 A1    Oct. 22, 2020

Related U.S. Application Data

(63) Continuation of application No. 16/014,326, filed on Jun. 21, 2018, now Pat. No. 10,743,743.

(30) Foreign Application Priority Data

Jul. 5, 2017 (JP) .............. JP2017-132244

(51) Int. Cl.
| | | |
|---|---|---|
| H04N 7/18 | (2006.01) | |
| A62B 1/04 | (2006.01) | |
| A61B 1/06 | (2006.01) | |
| A61B 1/00 | (2006.01) | |
| A61B 90/00 | (2016.01) | |
| A61B 1/04 | (2006.01) | |
| A61B 1/05 | (2006.01) | |

(52) U.S. Cl.
CPC ........ *A61B 1/0005* (2013.01); *A61B 1/00009* (2013.01); *A61B 1/0638* (2013.01); *A61B 90/361* (2016.02); *A61B 1/00048* (2013.01); *A61B 1/05* (2013.01); *A61B 2090/364* (2016.02)

(58) Field of Classification Search
USPC .................................. 348/61, 65, 73, 78, 79
See application file for complete search history.

(56) References Cited

U.S. PATENT DOCUMENTS

| | | | |
|---|---|---|---|
| 10,008,240 B2 | 6/2018 | Koide et al. | |
| 2014/0139678 A1 | 5/2014 | Moriarty et al. | |
| 2015/0124069 A1* | 5/2015 | Tsukamoto | ........ G06K 9/00604 348/78 |
| 2018/0032131 A1 | 2/2018 | Yasuda et al. | |
| 2020/0120308 A1* | 4/2020 | McMillan | .............. H04N 7/142 |

FOREIGN PATENT DOCUMENTS

| | | |
|---|---|---|
| JP | 2015093147 A | 5/2015 |
| JP | 2015-134039 | 7/2015 |
| JP | 2015156889 A | 9/2015 |
| JP | 2017070636 A | 4/2017 |
| WO | WO-2016158000 A | 10/2016 |

* cited by examiner

*Primary Examiner* — Daquan Zhao
(74) *Attorney, Agent, or Firm* — XSENSUS LLP (57) ABSTRACT

A medical observation apparatus includes: a display unit that displays thereon an observation image corresponding to a result of examination on a subject; a first camera that performs imaging of plural persons surrounding the subject, and outputs a surrounding image; a selecting unit that selects, based on the surrounding image, an indicator from the plural persons; a line of sight detecting unit that detects a line of sight of the indicator; and a display control unit that causes the display unit to display thereon a superimposed image having a pointer superimposed on the observation image, the pointer being at a position according to a destination of the line of sight of the indicator.

7 Claims, 9 Drawing Sheets

MEDICAL OBSERVATION APPARATUS

CROSS-REFERENCE TO RELATED APPLICATIONS

The present application is a continuation of U.S. application Ser. No. 16/014,326, filed Jun. 21, 2018, which claims priority to JP 2017-132244, filed Jul. 5, 2017, the entire contents of each are incorporated herein by reference.

BACKGROUND

The present disclosure relates to a medical observation apparatus.

In the medical field, medical observation apparatuses, which are for observation of the inside of subjects, such as humans, and surfaces of the subjects, have been known (see, for example, Japanese Patent Application Laid-open No. 2015-134039).

A medical observation apparatus (endoscope apparatus) described in Japanese Patent Application Laid-open No. 2015-134039 includes: an insertion portion that is inserted in a subject, and takes in a subject image inside the subject from a distal end thereof; a camera head that captures the subject image and outputs an image signal; a control device that processes the image signal and generates a video signal for display; and a display device that displays thereon an observation image based on the video signal.

When a surgery is performed by use of this medical observation apparatus, operators, such as a surgeon and an assistant, perform the surgery inside the subject with a surgical instrument, such as forceps, while checking the observation image in the subject displayed on the display device.

SUMMARY

During the surgery, between the operators, such as the surgeon and the assistant, one of the operators may indicate a position in the subject on the observation image, to the other operator. Further, an educator who is in a position to educate the operators, such as the surgeon and the assistant, may also indicate a position in the subject on the observation image, to the operators. In these cases, for example, a pointer on a screen of the display device may be positioned at a desired position on the observation image, by an input device, such as a keyboard, being operated.

However, if the input device is positioned in an unclean area, since the indicator (the operator or the educator) indicating a position in the subject is in a clean area, the indicator is unable to operate the input device. Therefore, the indicator needs to instruct, with the indicator's voice, a nurse or the like who is in the unclean area, to operate the input device. Further, even if the input device is positioned in the clean area, the indicator needs to operate the input device after putting down the surgical instrument, such as forceps, that the indicator has been holding.

Therefore, there is problem that the work of indicating a position in the subject on the observation image is complicated, and improvement in convenience is unable to be achieved.

A medical observation apparatus according to one aspect of the present disclosure includes: a display unit that displays thereon an observation image corresponding to a result of examination on a subject; a first camera that performs imaging of plural persons surrounding the subject, and outputs a surrounding image; a selecting unit that selects, based on the surrounding image, an indicator from the plural persons; a line of sight detecting unit that detects a line of sight of the indicator; and a display control unit that causes the display unit to display thereon a superimposed image having a pointer superimposed on the observation image, the pointer being at a position according to a destination of the line of sight of the indicator.

DETAILED DESCRIPTION

Hereinafter, by reference to the drawings, modes for carrying out the present disclosure (hereinafter, "embodiments") will be described. The present disclosure is not limited by the embodiments described below. Further, the same portions will be assigned with the same reference signs, throughout the drawings.

First Embodiment

Schematic Configuration of Medical Observation Apparatus

Figure 1:
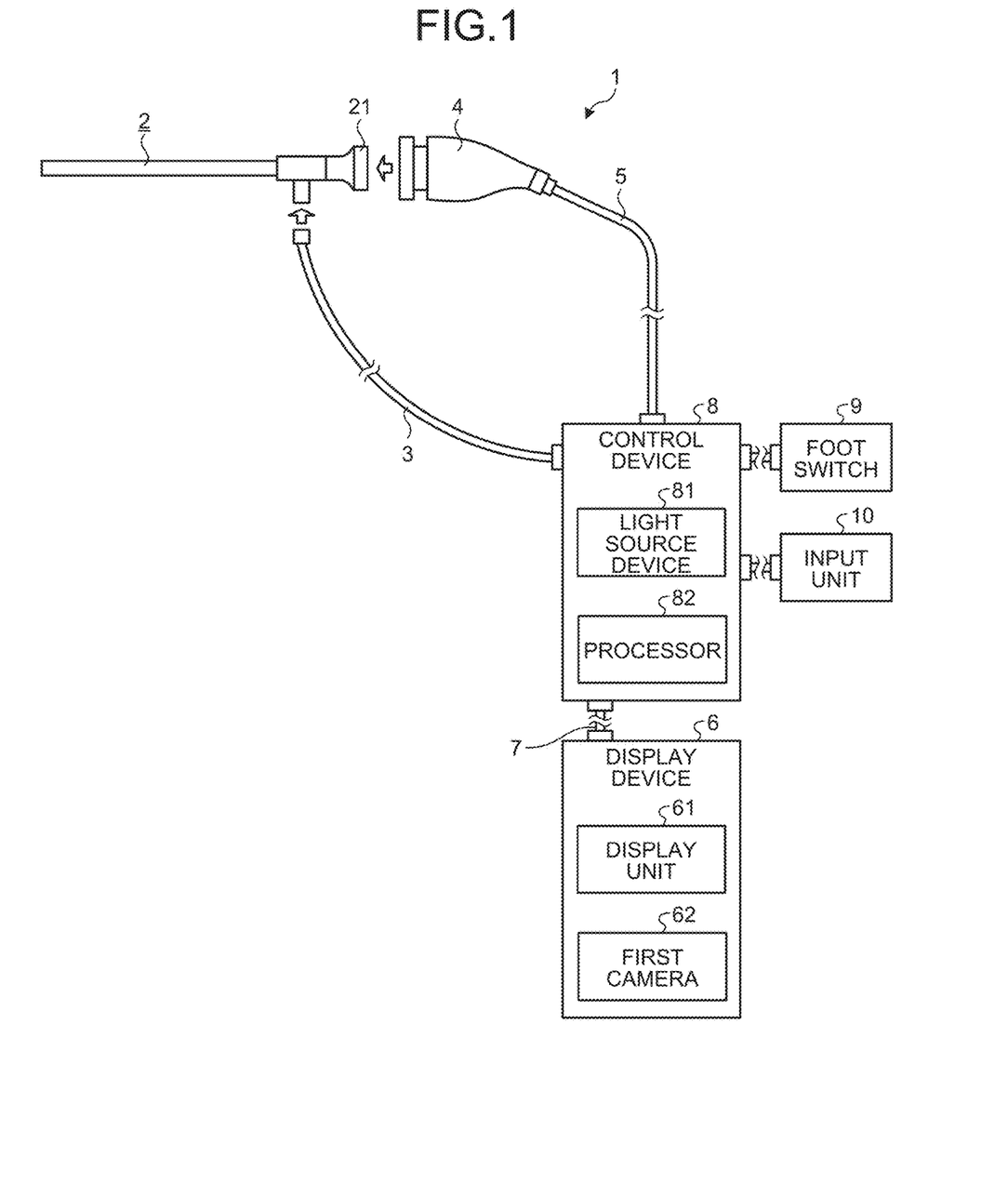
FIG. 1 is a diagram depicting a schematic configuration of a medical observation apparatus according to a first embodiment.

FIG. 1 is a diagram depicting a schematic configuration of a medical observation apparatus 1 according to a first embodiment.

The medical observation apparatus 1 is an apparatus that is used in the medical field, and for observation inside a living body. This medical observation apparatus 1 includes, as depicted in FIG. 1, an insertion portion 2, a light guide 3, a camera head 4, a first transmission cable 5, a display device 6, a second transmission cable 7, and a control device 8.

The insertion portion 2 is formed of a rigid endoscope. That is, the insertion portion 2 is rigid, or at least a part thereof is flexible, and the insertion portion 2 has an elongated shape, and is inserted in a living body. Provided in this insertion portion 2 is an optical system, which is formed by use of one lens or plural lenses, and which condenses a subject image.

One end of the light guide 3 is detachably connected to the control device 8, and the other end of the light guide 3 is detachably connected to the insertion portion 2. The light guide 3 transmits light supplied from the control device 8 from the one end to the other end, and supplies the light to the insertion portion 2. The light supplied to the insertion portion 2 is emitted from a distal end of the insertion portion 2, and emitted into the living body. The light emitted into the living body and reflected inside the living body (the subject image) is condensed by the optical system in the insertion portion 2.

The camera head 4 is a portion that is detachably connected to a proximal end (an eyepiece portion 21 (FIG. 1)) of the insertion portion 2, and is held by a user (scopist). The camera head 4 includes an imaging element (not depicted in the drawings), such as a charge coupled device (CCD) or a complementary metal oxide semiconductor (CMOS); and under control by the control device 8, captures a subject image condensed in the insertion portion 2, and outputs an image signal acquired by the capturing. The image signal is, for example, and an image signal of 4K or more.

The first transmission cable 5 has one end detachably connected to the control device 8 via a connector, and another end detachably connected to the camera head 4 via a connector. The first transmission cable 5 transmits the image signal output from the camera head 4, to the control device 8, and transmits each of a control signal, a synchronization signal, a clock, power, and the like output from the control device 8, to the camera head 4.

The transmission of the image signal to the control device 8 from the camera head 4 via the first transmission cable 5 may be transmission of the image signal through an optical signal, or transmission of the image signal through an electric signal. The same applies to the transmission of the control signal, the synchronization signal, and the clock, from the control device 8 to the camera head 4 via the first transmission cable 5.

The display device 6 includes, as depicted in FIG. 1, a display unit 61, and a first camera 62.

The display unit 61 is formed by use of a display using liquid crystal, organic electroluminescence (EL), or the like; and under control by the control device 8, the display unit 61 displays thereon an image based on a video signal from the control device 8.

Figure 4:
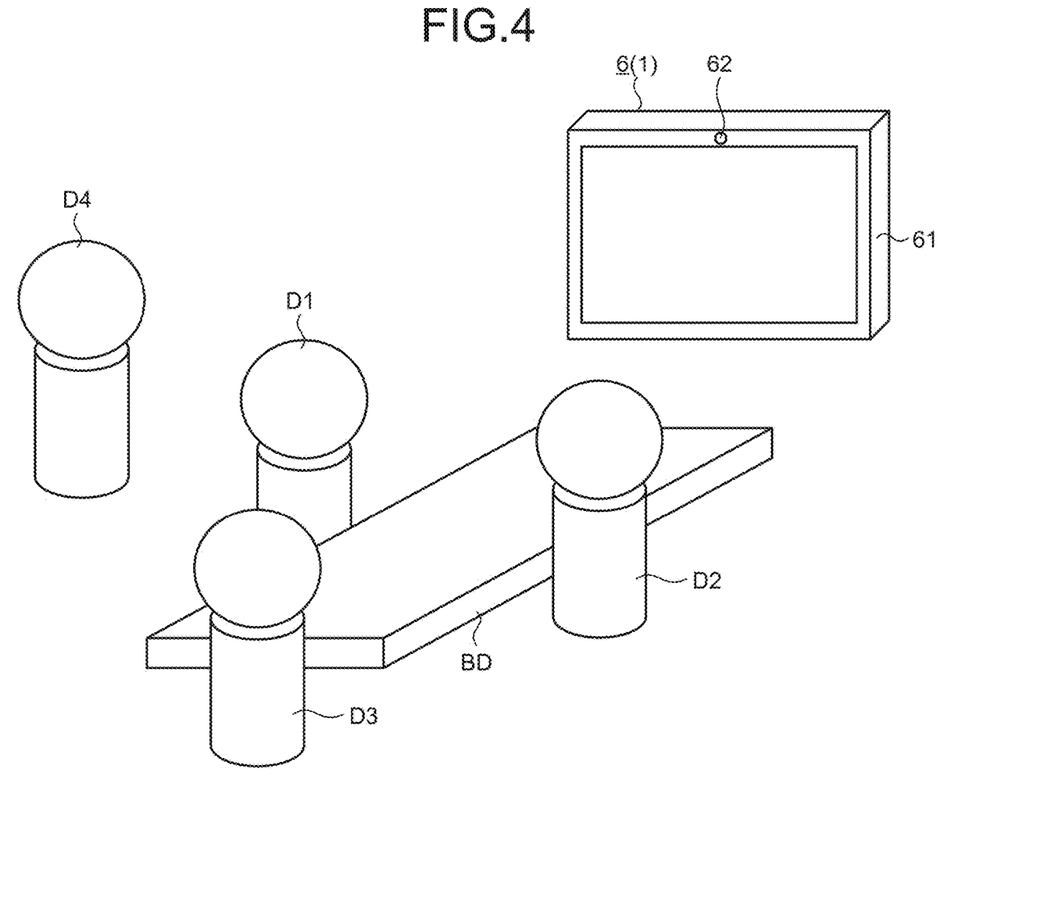
FIG. 4 is a diagram schematically depicting a situation in a surgery where the medical observation apparatus is used.

The first camera 62 is a camera, which includes an imaging element, such as a CCD or a CMOS, is fixed to the display unit 61, and has an imaging field in front of a screen of the display unit 61 (see FIG. 4). The first camera 62 captures an image in front of the screen of the display unit 61, and outputs an image signal acquired by the capturing.

One end of the second transmission cable 7 is detachably connected to the display device 6, and another end of the second transmission cable 7 is detachably connected to the control device 8. The second transmission cable 7 transmits the image signal output from the first camera 62, to the control device 8, and transmits a video signal processed in the control device 8, to the display unit 61.

The transmission of the image signal to the control device 8 from the first camera 62 via the second transmission cable 7 may be transmission of the image signal through an optical signal, or transmission of the image signal through an electric signal. The same applies to the transmission of the video signal from the control device 8 to the display unit 61 via the second transmission cable 7.

The control device 8 includes, as depicted in FIG. 1, a light source device 81 and a processor 82.

The light source device 81 supplies, under control by the processor 82, light for illuminating inside a living body, to the one end of the light guide 3.

The processor 82 is configured to include a central processing unit (CPU) or the like, and integrally controls operation of the light source device 81, the camera head 4, and the display device 6.

A detailed configuration of the processor 82 will be described later.

In this first embodiment, a configuration integral with a light source is adopted as the control device 8, the configuration having the light source device 81 and the processor 82 arranged in the same casing, but the first embodiment is not limited to this configuration, and the light source device 81 and the control device 8 may be provided separately.

Further, each of a foot switch 9 and an input unit 10 is connected, as depicted in FIG. 1, to the control device 8.

The foot switch 9 is a portion operated by a user with the user's foot, and outputs an operation signal corresponding to a user operation received, to the processor 82.

The input unit 10 is configured by use of, for example, a keyboard and a mouse, and outputs an operation signal corresponding to a user operation received, to the processor 82.

The foot switch 9 and the input unit 10 correspond to an operation receiving unit according to the present disclosure.

Configuration of Processor

Figure 2:
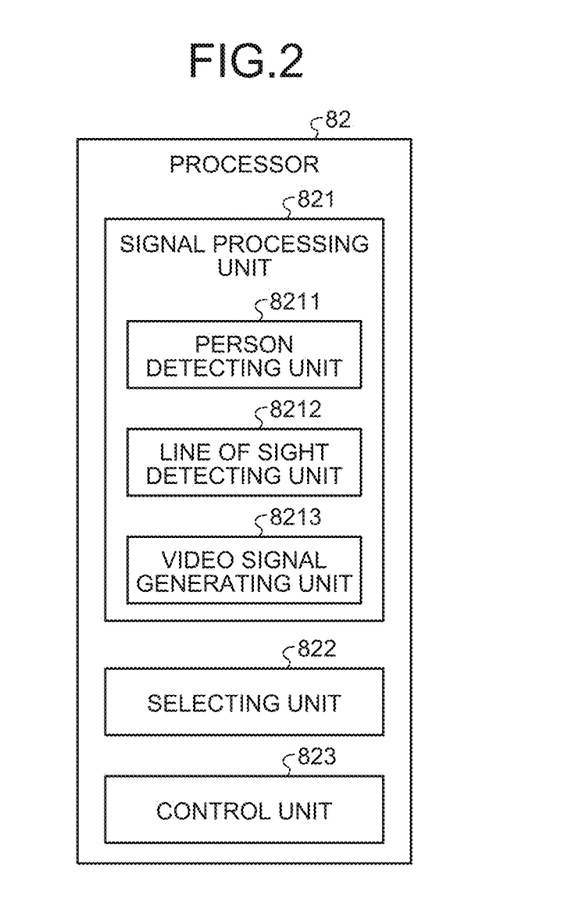
FIG. 2 is a block diagram depicting a configuration of a processor.

FIG. 2 is a block diagram depicting a configuration of the processor 82.

The processor 82 includes, as depicted in FIG. 2, a signal processing unit 821, a selecting unit 822, and a control unit 823.

The signal processing unit 821 processes, under control by the control unit 823, an image signal from the camera head 4 or an image signal from the first camera 62. Hereinafter, for distinguishment between an image signal from the camera head 4 and an image signal from the first camera 62, the image signal from the camera head 4 will be referred to as an observation image, and the image signal from the first camera 62 will be referred to as a surrounding image. This signal processing unit 821 includes, as depicted in FIG. 2, a person detecting unit 8211, a line of sight detecting unit 8212, and a video signal generating unit 8213.

The person detecting unit 8211 executes person detection processing of detecting an area (including an area representing an image of a face) by using feature data based on gradient information, feature data based on color information, feature data based on motion, and the like, the area representing an image of a person in the whole image area of a surrounding image.

Examples of the feature data based on gradient information include feature data on histograms of oriented gradients (HOG), and feature data on edge orientation histograms (EOH). Examples of the feature data based on color information include feature data on integral channel features (ICF), and color self similarity (CSS). Examples of the feature data based on motion include Haar-like feature data, and feature data on histograms of flow (HOF).

The line of sight detecting unit 8212 recognizes an area representing an image of a person (an indicator) selected by the selecting unit 822, from areas respectively representing images of plural persons detected by the person detecting unit 8211. The line of sight detecting unit 8212 then detects a line of sight of the indicator, by using the area representing the image of the indicator.

The video signal generating unit 8213 corresponds to a display control unit according to the present disclosure. This video signal generating unit 8213 generates a video signal corresponding to an image to be displayed on the display unit 61, outputs the video signal to the display unit 61 via the second transmission cable 7, and causes the display unit 61 to display thereon the image corresponding to the video signal.

For example, the video signal generating unit 8213 causes the display unit 61 to display thereon a superimposed image having a surrounding image superimposed, as well as a pointer superimposed, on an observation image, the pointer being at a position according to a destination of a line of sight of the indicator detected by the line of sight detecting unit 8212.

The selecting unit 822 selects, according to an operation signal from the input unit 10, an indicator from the plural persons detected by the person detecting unit 8211.

The control unit 823 is configured by use of a CPU or the like, and controls operation of the light source device 81, the camera head 4, and the display device 6, as well as operation of the whole processor 82.

Operation of Processor

Next, operation of the above described processor 82 will be described.

Figure 3:
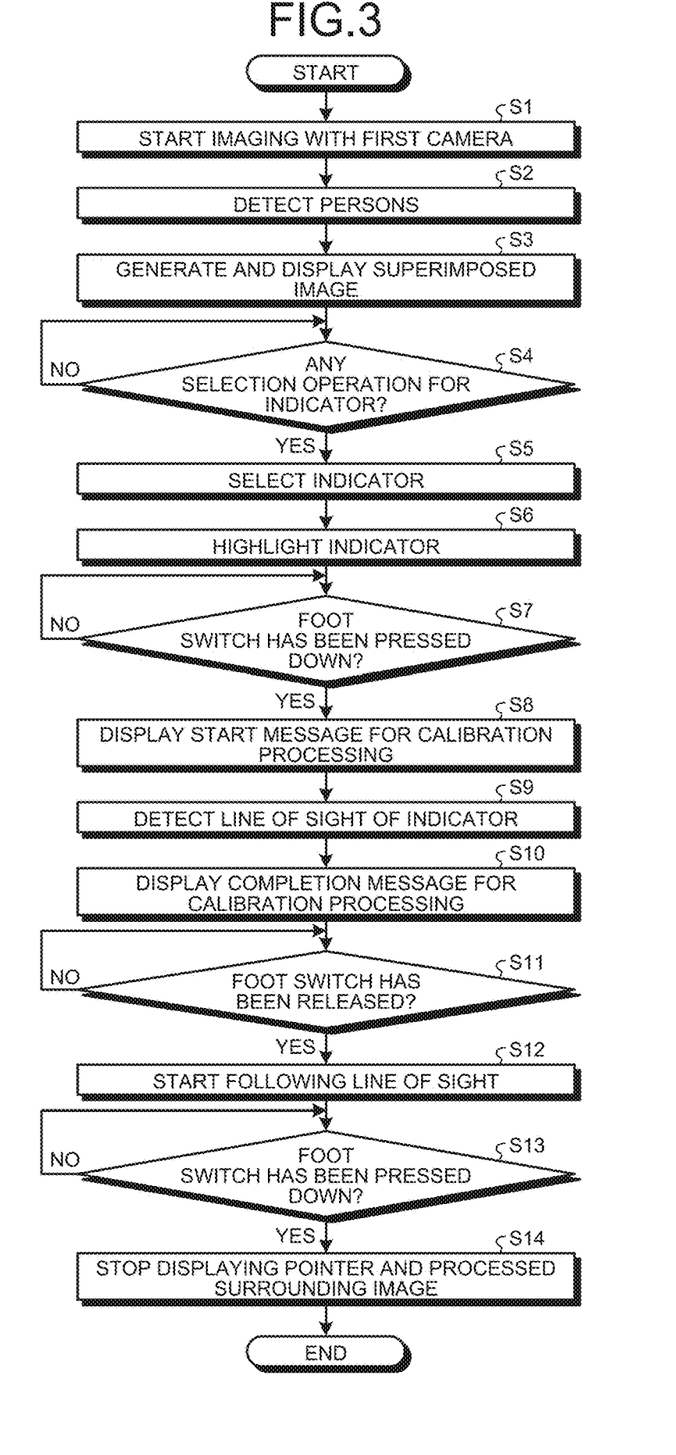
FIG. 3 is a flow chart depicting operation of the processor.

FIG. 3 is a flow chart depicting the operation of the processor 82. FIG. 4 is a diagram schematically depicting a situation in a surgery where the medical observation apparatus 1 is used. In FIG. 4, for convenience of explanation, only the display device 6 is depicted as the medical observation apparatus 1.

Hereinafter, the situation in the surgery depicted in FIG. 4 will be supposed. Specifically, as depicted in FIG. 4, around a surgery bed BD where a subject (not depicted in the drawings) is lying, four persons including a surgeon D1 and an assistant D2 who perform the surgery, a scopist D3 who holds the camera head 4, and an educator D4 who is in a position to educate the surgeon D1 and the assistant D2, are standing. Further, around the surgery bed BD, the display device 6 is arranged in a posture where its screen faces the surgery bed BD. The four persons D1 to D4 are checking an image being displayed on the display unit 61.

Firstly, the control unit 823 outputs a control signal to the first camera 62 via the second transmission cable 7, and causes the first camera 62 to start imaging (Step S1). The first camera 62 then performs imaging of the four persons D1 to D4 surrounding the subject (surgery bed BD), and outputs, via the second transmission cable 7, a surrounding image acquired by the imaging, to the signal processing unit 821.

After Step S1, the person detecting unit 8211 executes person detection processing, and detects areas respectively representing images of the four persons D1 to D4 included in the surrounding image (Step S2).

After Step S2, the video signal generating unit 8213 generates a processed surrounding image having first identification information superimposed on the surrounding image, the first identification information enabling the areas respectively representing the images of the four persons D1 to D4 detected by the person detecting unit 8211 to be identified. Further, the video signal generating unit 8213 generates a superimposed image having the processed surrounding image and a pointer superimposed on an observation image, and causes the display unit 61 to display thereon the superimposed image (Step S3).

Figure 5A:
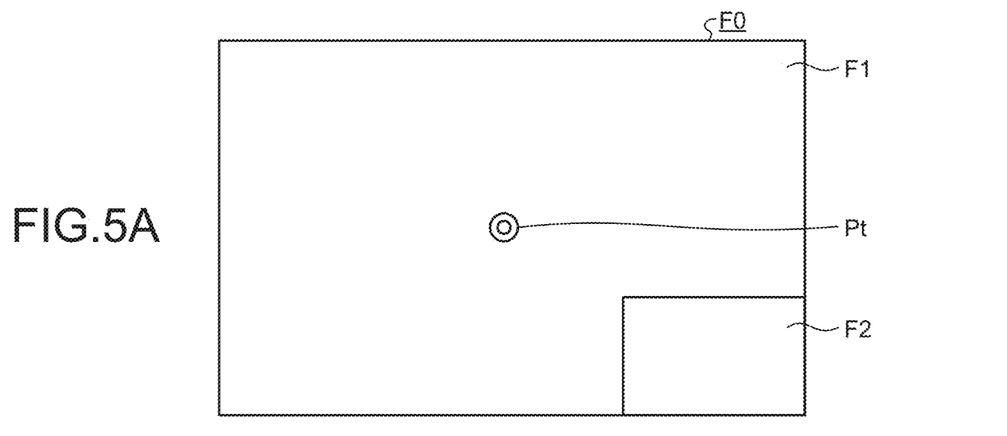
FIGS. 5A to 5C are diagrams depicting images displayed on a display unit.
Figure 5B:
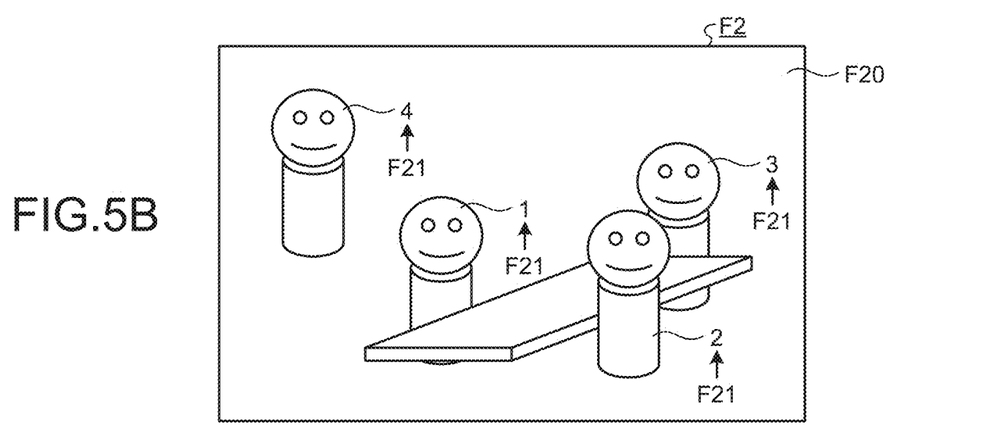
Figure 5C:
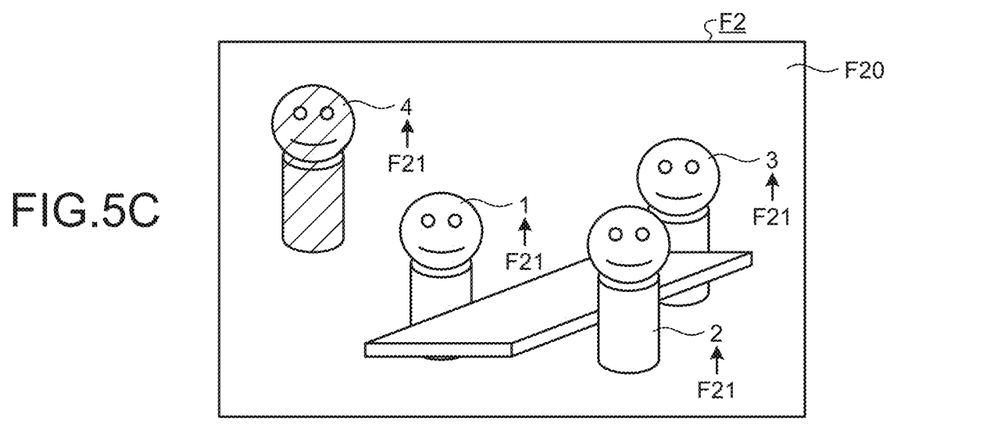

FIGS. 5A to 5C are diagrams depicting images displayed on the display unit 61. Specifically, FIG. 5A is a diagram depicting a superimposed image F0 displayed on the display unit 61 at Step S3. FIG. 5B is a diagram depicting a processed surrounding image F2 in the superimposed image F0. FIG. 5C is a diagram for explanation of Step S6 described later.

The superimposed image F0 is, as depicted in FIG. 5A, an image, having the processed surrounding image F2 and a pointer Pt superimposed on an observation image F1. Specifically, the observation image F1 is displayed on the whole screen of the display unit 61. Further, the processed surrounding image F2 is, as depicted in FIG. 5B, an image having first identification information F21 superimposed on the surrounding image F20. In the example of FIG. 5B and FIG. 5C: a character, "1", for the surgeon D1; a character, "2", for the assistant D2; a character, "3", for the scopist D3; and a character, "4", for the educator D4, are adopted as the first identification information F21. The processed surrounding image F2 is, as depicted in FIG. 5A, displayed in a right corner on the screen of the display unit 61. Further, the pointer Pt is, as depicted in FIG. 5A, displayed in the center of the screen of the display unit 61, at the time of Step S3.

After Step S3, the control unit 823 continuously monitors whether or not there has been any selection operation for an indicator on the input unit 10 (Step S4).

For example, any one of the four persons D1 to D4 in a clean area, or a person inputter, such as a nurse, in the clean area or an unclean area, checks the superimposed image F0 (processed surrounding image F2) being displayed on the display unit 61, and selects an indicator from the four persons D1 to D4 through an input operation on the input unit 10. In the example of FIG. 5B and FIG. 5C, when the surgeon D1 is made the indicator, the inputter inputs "1", which is the first identification information F21 in the superimposed image F0 assigned to the surgeon D1, through the input unit 10 (selection operation). Further, when the assistant D2 is made the indicator, the inputter inputs "2", which is the first identification information F21 in the superimposed image F0 assigned to the assistant D2, through the input unit 10 (selection operation). Furthermore, when the scopist D3 is made the indicator, the inputter inputs "3", which is the first identification information F21 in the superimposed image F0 assigned to the scopist D3 (selection operation). Moreover, when the educator D4 is made the indicator, the inputter inputs "4", which is the first identification information F21 in the superimposed image F0 assigned to the educator D4, through the input unit 10 (selection operation).

If it is determined that a selection operation for an indicator has been made on the input unit 10 (Step S4: Yes), the selecting unit 822 selects the indicator from the plural persons D1 to D4 detected by the person detecting unit 8211, according to an operation signal from the input unit 10 (Step S5).

After Step S5, the video signal generating unit 8213 highlights the indicator, as depicted in FIG. 5C, to enable the indicator selected by the selecting unit 822 and the other persons, among the plural persons D1 to D4, to be distinguished from each other on the processed surrounding image F2 (Step S6). In FIG. 5C, the highlight is expressed by oblique lines. Further, FIG. 5C exemplifies a case where the educator D4 has been set as the indicator at Step S5.

After Step S6, the control unit 823 continuously monitors whether or not the foot switch 9 has been pressed down (Step S7).

If it is determined that the foot switch 9 has been pressed down (Step S7: Yes), the video signal generating unit 8213 causes the display unit 61 to display thereon an image having a start message for calibration processing superimposed on the superimposed image F0 (Step S8).

Examples of the start message for calibration processing include a message, "Calibration processing will now be started. The indicator is asked to continue looking at the pointer in the center of the screen.". The indicator then checks the message displayed on the display unit 61, and continues to look at the pointer Pt positioned in the center of the screen of the display unit 61.

Figure 6A:
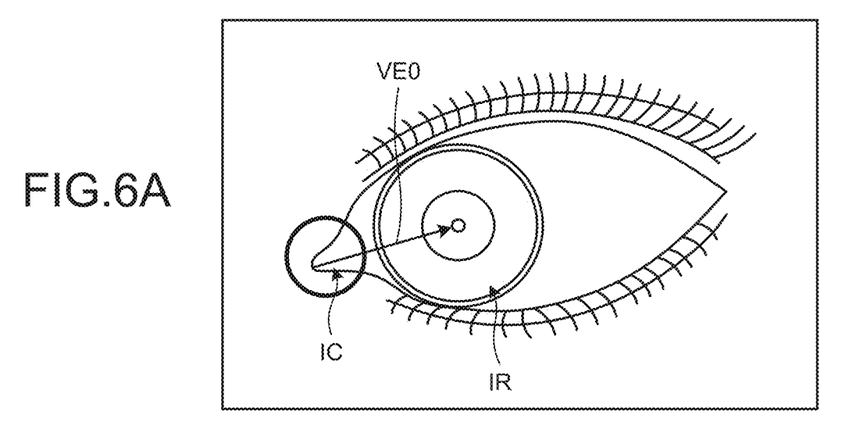
FIGS. 6A and 6B are diagrams for explanation of Steps S9 and S12.
Figure 6B:
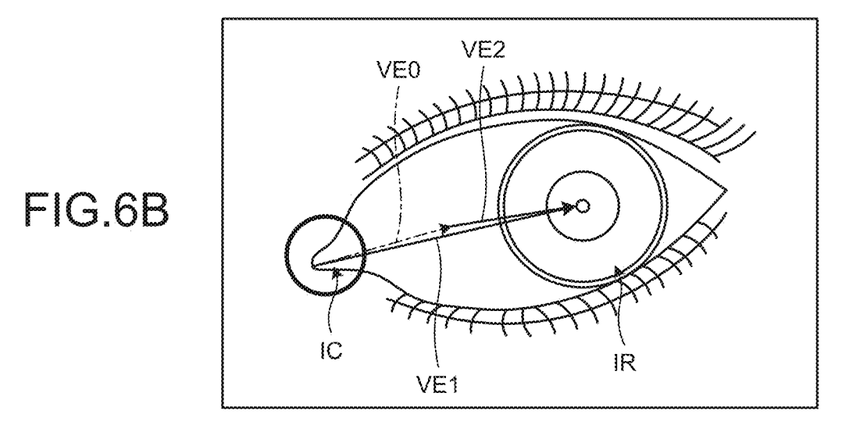

FIGS. 6A and 6B are diagrams for explanation of Steps S9 and S12.

After Step S8, the line of sight detecting unit 8212 recognizes an area representing an image of the indicator, from the areas respectively representing the images of the plural persons D1 to D4 detected by the person detecting unit 8211. The line of sight detecting unit 8212 then detects a line of sight, along which the indicator is looking at the pointer Pt positioned in the center of the screen of the display unit 61, by using the area representing the image of the indicator (Step S9).

For example, the line of sight detecting unit 8212 calculates, at Step S9, as depicted in FIG. 6A, a reference line of sight vector VE0 from an area representing an image of an inner corner IC of an eye of the indicator looking at the pointer Pt positioned in the center of the screen of the display unit 61 to an area representing an image of an iris IR thereof.

After Step S9, the video signal generating unit 8213 causes the display unit 61 to display thereon an image without the start message for calibration processing being displayed and having a completion message for calibration processing superimposed on the superimposed image F0 (Step S10).

Examples of the completion message for calibration processing include, for example, a message, "Calibration processing has been completed.". The indicator then checks the message displayed on the display unit 61, takes the indicator's eyes off the pointer Pt positioned in the center of the screen of the display unit 61, and takes the indicator's foot away from the foot switch 9 the indicator has been pressing down since Step S7.

After Step S10, the control unit 823 continuously monitors whether or not the foot switch 9 has been released (the foot that has been pressing down the foot switch 9 has been taken off) (Step S11).

If it is determined that the foot switch 9 has been released (Step S11: Yes), the line of sight detecting unit 8212 starts following the line of sight of the indicator (Step S12).

For example, the line of sight detecting unit 8212 calculates, at Step S12, as depicted in FIG. 6B, similarly to Step S9, a line of sight vector VE1 from an area representing an image of the inner corner IC of the eye of the indicator to an area representing an image of the iris IR thereof. The line of sight detecting unit 8212 calculates, based on the reference line of sight vector VE0 calculated at Step S9 and the calculated line of sight vector VE1, a motion vector VE2 of the iris IR. The motion vector VE2 is a vector indicating how much the iris IR moved in which direction, with reference to the position of the iris IR of the indicator looking at the pointer Pt positioned in the center of the screen of the display unit 61. Therefore, by the pointer Pt being moved from the position in the center of the screen of the display unit 61 in the direction and by the amount according to the motion vector VE2, the pointer Pt is able to be positioned at the destination of the line of sight of the indicator. The video signal generating unit 8213 then moves, based on the motion vector VE2, the pointer Pt in the superimposed image F0. That is, the pointer Pt moves, following the line of sight of the indicator.

After Step S12, the control unit 823 continuously monitors whether or not the foot switch 9 has been pressed down again (Step S13).

If it is determined that the foot switch 9 has been pressed down again (Step S13: Yes), the video signal generating unit 8213 stops displaying the pointer Pt and the processed surrounding image F2 in the superimposed image F0 (Step S14). That is, only the observation image F1 is displayed on the display unit 61.

The above described first embodiment has the following effects.

The medical observation apparatus 1 according to the first embodiment performs imaging of plural persons (four persons D1 to D4 in the example of FIG. 4) surrounding a subject, and based on the surrounding image F20 acquired by the imaging, selects an indicator from the plural persons. The medical observation apparatus 1 then detects a line of sight of the indicator, and displays the superimposed image F0 having the pointer Pt superimposed on the observation image F1, the pointer Pt being at a position according to a destination of the line of sight of the indicator.

Therefore, the indicator is able to position the pointer Pt on the screen of the display unit 61 at a desired position, just by changing the indicator's line of sight. Therefore, the medical observation apparatus 1 according to the first embodiment has an effect of enabling a desired position on the observation image F1 to be easily indicated, and enabling improvement in convenience.

Further, the medical observation apparatus 1 according to the first embodiment detects, based on the surrounding image F20 generated by imaging with the first camera 62, a line of sight of the indicator.

Therefore, there is no need for a camera to be separately provided for the detection of the line of sight of the indicator, and just with the first camera 62 that generates the surrounding image D20, the selection of the indicator and the detection of the line of sight of the indicator are able to be performed. Therefore, reduction in cost of the medical observation apparatus 1 is able to be achieved.

Further, the medical observation apparatus 1 according to the first embodiment displays the superimposed image F0 having, in addition to the pointer Pt, the processed surrounding image F2 superimposed on the observation image F1, the processed surrounding image F2 enabling the indicator and the other persons among the plural persons to be distinguished from each other.

Therefore, by checking the processed surrounding image F2 displayed on the display unit 61 (by checking the highlighted person among the plural persons D1 to D4 in the example of FIG. 5C), the plural persons are able to easily recognize who the indicator is.

Further, the medical observation apparatus 1 according to the first embodiment displays the superimposed image F0 having, in addition to the pointer Pt, the processed surrounding image F2 superimposed on the observation image F1, the processed surrounding image F2 having the first identification information F21 assigned to each of the plural persons.

Therefore, by checking the processed surrounding image F2 (first identification information F21) displayed on the display unit 61, an inputter selecting an indicator from the plural persons is able to easily perform a selection operation for the indicator on the input unit 10 (the operation of inputting any one of "1" to "4" that are the first identification information F21 in the example of FIG. 5B).

Further, the medical observation apparatus 1 according to first embodiment switches between display and non-display of the pointer Pt and the processed surrounding image F2, according to a user operation on the foot switch 9.

Therefore, it is possible: for the pointer Pt and the processed surrounding image F2 to be displayed only when the indication is performed, and for only the observation image F1 to be displayed when the indication is not performed.

Second Embodiment

Next, a second embodiment will be described.

In the following description, any component that is the same as that of the above described first embodiment will be assigned with the same reference sign, and detailed description thereof will be omitted or simplified.

The above described medical observation apparatus 1 according to the first embodiment is configured to be used for 2D observation where the observation image F1 is displayed as a two-dimensional (2D) image and a user performs 2D observation.

In contrast, a medical observation apparatus according to this second embodiment is configured to be used for 3D observation where an observation image F1 is displayed as a three-dimensional (3D) image and a user performs stereoscopic observation.

Figure 7:
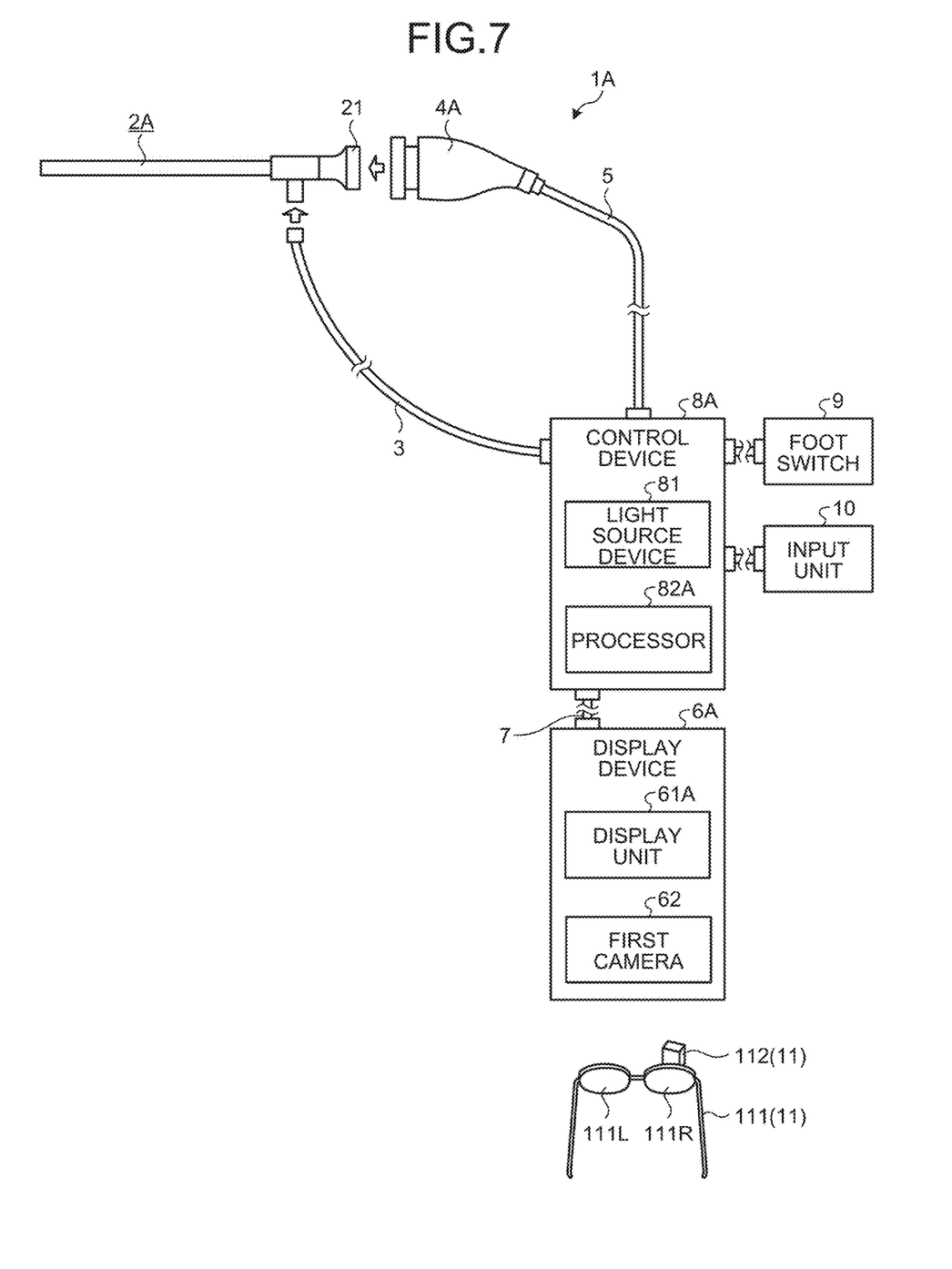
FIG. 7 is a diagram depicting a schematic configuration of a medical observation apparatus according to a second embodiment.

FIG. 7 is a diagram depicting a schematic configuration of a medical observation apparatus 1A according to the second embodiment.

The medical observation apparatus 1A according to the second embodiment: respectively has, as depicted in FIG. 7, an insertion portion 2A, a camera head 4A, a display device 6A, and a control device 8A, which are for use in 3D observation, adopted therein, instead of the insertion portion 2, the camera head 4, the display device 6, and the control device 8; and has stereoscopic observation glasses 11 added therein, in contrast to the above described medical observation apparatus 1 according to the first embodiment.

In FIG. 7, for convenience of explanation, only one pair of stereoscopic observation glasses 11 is depicted, but plural pairs of the stereoscopic observation glasses 11 (four for the persons D1 to D4 in the example of FIG. 4) are provided.

The insertion portion 2A is formed of a scope of the binocular relay type or the monocular pupil-division type.

Specifically, the scope of the binocular relay type has two optical paths juxtaposed in the scope. Further, each of the two optical paths has an optical system arranged therein. In the scope of the binocular relay type, the two optical systems respectively take in and emit left eye observation light and right eye observation light having a parallax therebetween (for example, see Japanese Patent Application Laid-open No. H06-160731).

Furthermore, the scope of the monocular pupil-division type has one optical path provided in the scope. Moreover, the one optical path has an optical system arranged therein. What is more, at a pupil position of the optical system, a pupil division unit that divides luminous flux in the pupil into two regions is provided. The scope of the monocular pupil-division type takes in observation light through the optical system, and separates and emits the observation light into left eye observation light and right eye observation light through the pupil division unit (see, for example, Japanese Patent Application Laid-open No. H06-059199).

Under control by the control device 8A, the camera head 4A generates a left eye image signal by imaging the left eye observation light condensed in the insertion portion 2A, and generates a right eye image signal by imaging the right eye observation light condensed in the insertion portion 2A. The camera head 4A then outputs the left and right eye image signals to the control device 8A via the first transmission cable 5.

The display device 6A has a display unit 61A for use in 3D observation, instead of the display unit 61, in contrast to the above descried display device 6 according to the first embodiment.

The display unit 61A is formed of a 3D display of the active type or the passive type, and displays thereon a three-dimensional image based on a three-dimensional video signal processed in the control device 8A.

The control device 8A has a processor 82A for use in 3D observation, instead of the processor 82, in contrast to the above described control device 8 according to the first embodiment.

Figure 8:
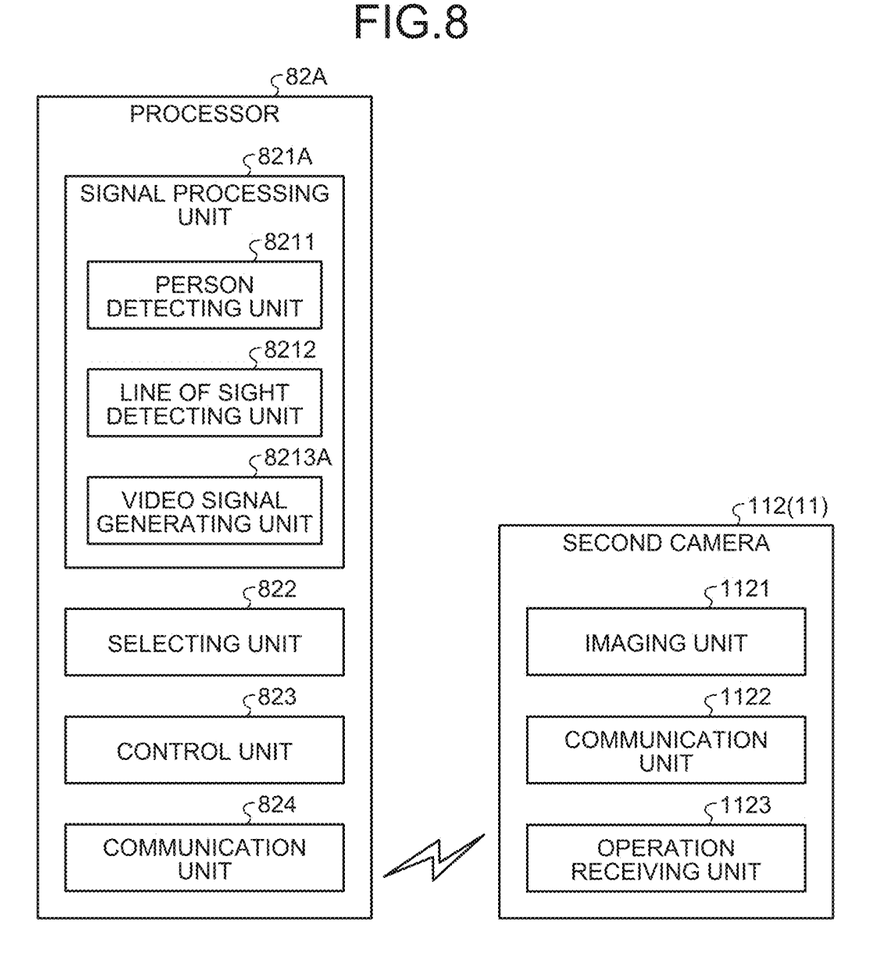
FIG. 8 is a block diagram depicting a configuration of a processor and a second camera.

FIG. 8 is a block diagram depicting a configuration of the processor 82A and a second camera 112.

The processor 82A has, instead of the signal processing unit 821 (video signal generating unit 8213), a signal processing unit 821A adopted therein, and a communication unit 824 added therein, in contrast to the above described processor 82 according to first embodiment, the signal processing unit 821A having a video signal generating unit 8213A for use in 3D observation installed therein.

The video signal generating unit 8213A corresponds to a display control unit according to the present disclosure. This video signal generating unit 8213A generates a three-dimensional video signal corresponding to a three-dimensional image to be displayed on the display unit 61A, outputs the three-dimensional video signal to the display unit 61A via the second transmission cable 7, and causes the display unit 61A to display thereon the three-dimensional image corresponding to the three-dimensional video signal.

For example, the video signal generating unit 8213A generates a left eye superimposed image having a surrounding image and a pointer superimposed on a left eye image signal (a left eye observation image) from the camera head 4A. Further, the video signal generating unit 8213A generates a right eye superimposed image having a surrounding image and a pointer superimposed on a right eye image signal (a right eye observation image) from the camera head 4A. The video signal generating unit 8213A then causes the display unit 61A to display thereon a three-dimensional image based on the left and right superimposed images.

The video signal generating unit 8213A executes the same processing as the above described video signal generating unit 8213 according to first embodiment (Steps S3, S6, S8, S10, S12, and S14), except that the superimposed image F0 (observation image F1) is generated as a three-dimensional image.

The communication unit 824 performs wireless communication with the stereoscopic observation glasses 11 (second camera 112).

The stereoscopic observation glasses 11 are worn by a user (in the example of FIG. 4, the four persons D1 to D4) who stereoscopically sees the three-dimensional image displayed on the display unit 61A. The stereoscopic observation glasses 11 include, as depicted in FIG. 7 or FIG. 8, 3D glasses 111 and the second camera 112.

The 3D glasses 111 are formed as 3D glasses of the active type or the passive type, and includes, as depicted in FIG. 7: a left light guiding section 111L that guides the left eye superimposed image (the left eye observation image if the surrounding image and the pointer are not displayed) of the three-dimensional image displayed on the display unit 61A, to a left eye; and a right light guiding section 111R that guides the right eye superimposed image (the right eye observation image if the surrounding image and the pointer are not displayed) of the three-dimensional image, to a right eye. A user who has worn the 3D glasses 111 stereoscopically sees the three-dimensional image displayed on the display unit 61A, by visually recognizing the left and right eye superimposed images having a parallax therebetween respectively with the user's left and right eyes.

The second camera 112 is attached to the 3D glasses 111 (above the right light guiding section 111R in the example of FIG. 7). This second camera 112 includes, as depicted in FIG. 8, an imaging unit 1121, a communication unit 1122, and an operation receiving unit 1123.

The imaging unit 1121 includes an imaging element (not depicted in the drawings), such as a CCD or a CMOS, and captures an image of an eye (the right eye, in the example of FIG. 7) of the user who has worn the 3D glasses 111.

The communication unit 1122 performs wireless communication with the communication unit 824.

The operation receiving unit 1123 is formed of, for example, a push button switch, and is a portion that receives operation by the user wearing the 3D glasses 111.

According to this second embodiment, examples of a start message for calibration processing to be displayed on the display unit 61A at Step S8 include a message, "Calibration processing will now be started. The indicator is asked to perform operation on the 3D glasses and continue looking at the pointer in the center of the screen." The indicator then checks the message displayed on the display unit 61A, performs operation on the operation receiving unit 1123 of the stereoscopic observation glasses 11 that the indicator is wearing, and continues to look at the pointer Pt positioned in the center of the screen of the display unit 61A.

According to the operation on the operation receiving unit 1123, the communication unit 1122 transmits an image signal (corresponding to an image for detection according to the present disclosure) acquired by the imaging by the imaging unit 1121, to the communication unit 824. At Steps S9 and S12, the line of sight detecting unit 8212 detects, based on the image for detection received by the communication unit 824, a line of sight of the indicator.

Even if the present disclosure is applied to use in 3D observation like the above described second embodiment, effects similar to those of the above described first embodiment are achieved.

Further, the medical observation apparatus 1A according to the second embodiment includes, separately from the first camera 62, the second camera 112 for the detection of a line of sight of an indicator. The second camera 112 is provided in the 3D glasses 111 worn by the indicator.

Therefore, since a line of sight of an indicator is able to be detected based on an image for detection having only an eye of the indicator captured therein, as compared to a case where the line of sight of the indicator is detected based on a surrounding image, the detection of the line of sight is able to be executed highly accurately.

Third Embodiment

Next, a third embodiment will be described.

In the following description, any component that is the same as that of the above described first embodiment will be assigned with the same reference sign, and detailed description thereof will be omitted or simplified.

In the above described medical observation apparatus 1 according to the first embodiment, only one person is selectable as an indicator.

In contrast, a medical observation apparatus according to this third embodiment is configured to enable plural persons to be selected as indicators.

The medical observation apparatus according to this third embodiment has a configuration that is the same as that of the above described medical observation apparatus 1 according to the first embodiment.

Figure 9A:
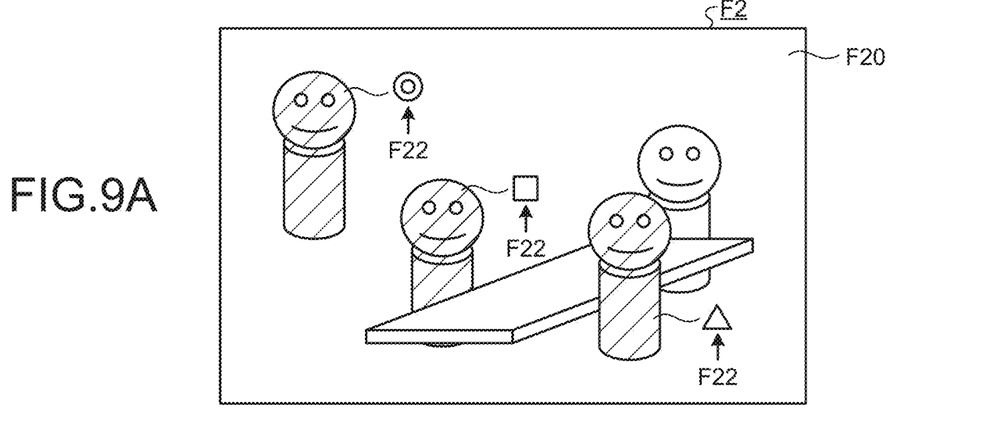
FIGS. 9A and 9B are diagrams depicting images displayed on a display unit according to a third embodiment.
Figure 9B:
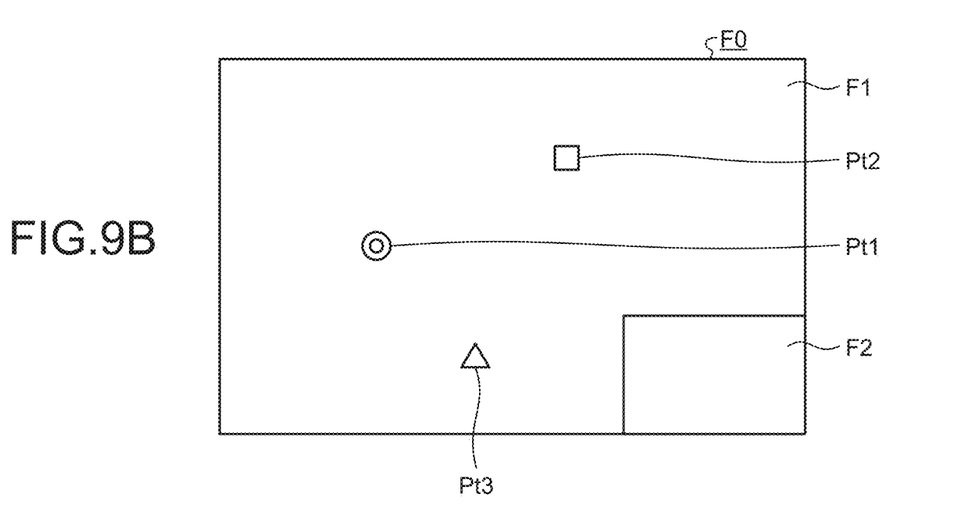

FIGS. 9A and 9B are diagrams depicting images displayed on the display unit 61 according to the third embodiment. Specifically, FIG. 9A is a diagram corresponding to FIG. 5C, and is a diagram for explanation of Step S6 according to this third embodiment. FIG. 9B is a diagram for explanation of Step S12 according to this third embodiment.

In this third embodiment, at Step S4, an inputter checks the superimposed image F0 (FIG. 5A) being displayed on the display unit 61 through input operation on the input unit 10, and selects plural indicators through input operation on the input unit 10. In the example of FIG. 9A, the inputter inputs "1", "2", and "4", that are the first identification information F21 (FIG. 5B) in the superimposed image F0 assigned to the surgeon D1, the assistant D2, and the educator D4, through the input unit 10, in order to select the three persons D1, D2, and D4, who are the surgeon D1, the assistant D2, and the educator D4, as the indicators (selection operation). The selecting unit 822 then selects, according to an operation signal from the input unit 10, plural indicators (the three persons D1, D2, and D4, in the example of FIG. 9A) from the plural persons D1 to D4 detected by the person detecting unit 8211 (Step S5).

Further, in this third embodiment, at Step S6, the video signal generating unit 8213 highlights the indicators to enable the indicators selected by the selecting unit 822 and the other persons to be distinguished from each other, among the plural persons D1 to D4, in the processed surrounding image F2. In FIG. 9A, the highlight is expressed by oblique lines. Further, as depicted in FIG. 9A, the video signal generating unit 8213 deletes the first identification information F21 from the processed surrounding image F2, and displays second identification information F22 enabling each of the plural indicators to be identified. In the example of FIG. 9A, as the second identification information F22, a "square" mark for the surgeon D1, a "triangle" mark for the assistant D2, and a "double circle" mark for the educator D4, are adopted.

Further, in this third embodiment, at Step S12, the video signal generating unit 8213 enables each of pointers corresponding to lines of sight of the plural indicators to be identified, and moves the pointers by respectively causing the pointers to follow the lines of sight of the plural indicators detected by the line of sight detecting unit 8212. In the example of FIG. 9B, a "square" mark similar to that of the second identification information F22 is adopted as a pointer Pt2 corresponding to the line of sight of the surgeon D1, a "triangle" mark similar to that of the second identification information F22 is adopted as a pointer Pt3 corresponding to the assistant D2, and a "double circle" mark is adopted as a pointer Pt1 corresponding to the educator D4.

According to the above described third embodiment, in addition to effects similar to those of the above described first embodiment, by selection of plural indicators being enabled, positions indicated by the plural indicators are able to be checked through an image displayed on the display unit 61, and thus improvement in convenience is able to be achieved even more.

Other Embodiments

Thus far, modes for carrying out the present disclosure have been described, but the present disclosure is not to be limited only to the above described first to third embodiments.

The medical observation apparatuses according to the above described first to third embodiments are configured as rigid endoscope apparatuses, in which the insertion portions 2 are each formed of a rigid endoscope, but not being limited to this configuration, a medical observation apparatus according to the present disclosure may be formed of a flexible endoscope apparatus, in which the insertion portion 2 is formed of a flexible endoscope. Further, a medical observation apparatus according to the present disclosure may be configured as, not necessarily an endoscope apparatus, but a surgical microscope (see, for example, Japanese Patent Application Laid-open No. 2016-042981), through which observation is performed by enlargement of a predetermined field area in a subject (in a living body) or on a surface of the subject (a surface of the living body).

In the above described first to third embodiments, at least a part of the components provided in the processor 82 or 82A (for example, the signal processing unit 821 or 821A) may be provided in the display device 6 or 6A. Further, the first camera 62 provided in the display device 6 or 6A may be provided independently of the display device 6 or 6A.

In the above described first to third embodiments, indicators are selected by selection operation on the input unit 10 by an inputter, but not being limited thereto, a configuration, in which an indicator is selected by image processing on a surrounding image, may be adopted. For example, an image of a face of a predetermined indicator (a pattern image) is stored beforehand in a memory in the processor 82 or 82A. By pattern matching or the like, a face matching the pattern image in a surrounding image is searched for, and a person corresponding to the face is selected as an indicator. Further, for example, a predetermined gesture (for example, a V-sign) is stored beforehand in a memory in the processor 82 or 82A. By pattern matching or the like, a person making that gesture in a surrounding image is searched for, and that person is selected as an indicator.

As to the user operation on the foot switch 9 also, Steps S8, S12, and S14 may be executed according to processing results of image processing on a surrounding image.

A medical observation apparatus according to the present disclosure performs imaging of plural persons surrounding a subject, and based on a surrounding image acquired by the imaging, selects an indicator from the plural persons. The medical observation apparatus then detects a line of sight of the indicator, and displays a superimposed image having a pointer superimposed on an observation image, the pointer being at a position according to a destination of the line of sight of the indicator.

Thus, the indicator is able to position the pointer on a screen of a display unit at a desired position, just by changing the indicator's line of sight. Therefore, the medical observation apparatus according to the present disclosure has an effect of enabling a desired position on an observation image to be easily indicated, and enabling improvement in convenience.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical observation apparatus, comprising:
   a medical camera configured to obtain an observation image of a patient;
   circuitry configured to:
   display on a display the observation image;
   detect a line of sight of an indicator, wherein the indicator is a user who provides an indication;
   display on the display a superimposed image comprising a pointer superimposed on the observation image, the pointer being at a position according to a destination of the line of sight of the indicator; and
   select, based on the surrounding image, the indicator from the plural users,
   wherein the superimposed image further comprises the surrounding image superimposed on the observation image, and the surrounding image distinguishes the indicator from others of the plural users.

2. The medical observation apparatus according to claim 1, wherein the circuitry is further configured to:
   obtain a surrounding image of plural users surrounding the patient with a first camera, and output the surrounding image.

3. The medical observation apparatus according to claim 2, wherein a first camera is configured to obtain the surrounding image from an imaging field in front of a screen of the display.

4. The medical observation apparatus according to claim 2 wherein the circuitry is further configured to:
   receive a user operation; and
   switch a display state of causing the display to display thereon the pointer and the surrounding image to a non-display state, in which the observation image is displayed and the pointer and the surrounding image are not displayed, according to the user operation.

5. The medical observation apparatus according to claim 1, wherein the circuitry is further configured to:
   detect the line of site of the indicator using glasses worn by the indicator.

6. A medical observation apparatus, comprising:
   a medical camera configured to obtain an observation image of a patient;
   circuitry configured to:
   display on a display the observation image;
   detect a line of sight of an indicator, wherein the indicator is a user who provides an indication;
   display on the display a superimposed image comprising a pointer superimposed on the observation image, the pointer being at a position according to a destination of the line of sight of the indicator;
   store an image of the indicator's face in a memory; and
   select the indicator from plural users by pattern matching the image of the indicator's face with the surrounding image.

7. A medical observation apparatus, comprising:
   a medical camera configured to obtain an observation image of a patient;
   circuitry configured to:
   display on a display the observation image;
   detect a line of sight of an indicator, wherein the indicator is a user who provides an indication;
   display on the display a superimposed image comprising a pointer superimposed on the observation image, the pointer being at a position according to a destination of the line of sight of the indicator;
   store a predetermined gesture in a memory;
   select the indicator from plural users by pattern matching the predetermined gesture with the surrounding image.

* * * * *